US008522585B1

(12) United States Patent  
Pratt et al.

(10) Patent No.: US 8,522,585 B1  
(45) Date of Patent: Sep. 3, 2013

(54) METHODS OF MAINTAINING AND USING A HIGH CONCENTRATION OF DISSOLVED COPPER ON THE SURFACE OF A USEFUL ARTICLE

(75) Inventors: Richard Pratt, Mt. Vernon, IA (US); Thomas D. Johnson, Marion, IA (US); Timothy Suh, Cedar Rapids, IA (US)

(73) Assignee: PMX Industries Inc., Cedar Rapids, IA (US)

( * ) Notice: Subject to any disclaimer, the term of this patent is extended or adjusted under 35 U.S.C. 154(b) by 1444 days.

(21) Appl. No.: 11/751,507

(22) Filed: May 21, 2007

Related U.S. Application Data

(60) Provisional application No. 60/747,948, filed on May 23, 2006.

(51) Int. Cl.
| | |
|---|---|
| B21C 43/00 | (2006.01) |
| A01N 59/20 | (2006.01) |
| A01N 59/16 | (2006.01) |
| A01N 25/00 | (2006.01) |
| A61K 33/34 | (2006.01) |
| A61K 33/24 | (2006.01) |

(52) U.S. Cl.  
USPC .............. 72/39; 424/630; 424/617; 424/405

(58) Field of Classification Search  
USPC .............. 72/39; 427/11; 424/630, 617, 405  
See application file for complete search history.

(56) References Cited

U.S. PATENT DOCUMENTS

| 4,247,374 A * | 1/1981 | Ruscoe et al. ............... 72/359 |
| 4,510,018 A | 4/1985 | McGowan |
| 4,644,674 A | 2/1987 | Burrows et al. |
| 4,946,520 A * | 8/1990 | Escobar et al. ................... 72/39 |
| 4,987,036 A | 1/1991 | Miller |
| 5,066,328 A | 11/1991 | Zlotnik |
| 5,171,350 A | 12/1992 | Stainer |
| 5,338,319 A | 8/1994 | Kaschig et al. |
| 5,861,068 A * | 1/1999 | Hasegawa et al. ............ 148/326 |
| 5,997,712 A | 12/1999 | Ting et al. |
| 6,042,877 A | 3/2000 | Lyon et al. |
| 6,080,497 A | 6/2000 | Carey, II et al. |
| 6,180,162 B1 * | 1/2001 | Shigeru et al. .................. 427/11 |
| 6,217,780 B1 | 4/2001 | Denkewicz, Jr. et al. |
| 6,313,064 B1 | 11/2001 | Miyafuji et al. |
| 6,458,222 B1 | 10/2002 | Matsubara et al. |
| 6,585,813 B2 | 7/2003 | Kiik et al. |
| 6,605,204 B1 | 8/2003 | Martyak et al. |

(Continued)

OTHER PUBLICATIONS

Gustavo Faundez, Miriam Troncoso, Paola Navarrete and Guillermo Figueroa, research article entitled Antimicrobial activity of copper surfaces against suspensions of *Salmonella enterica* and *Campylobacter jejun*, published Apr. 30, 2004 by BMC Microbiology, pp. 1-7.

Discover Copper: Oct. 2004. "An Important New Ally in Fight Against Germs".

(Continued)

*Primary Examiner* — Dana Ross  
*Assistant Examiner* — Mohammad I Yusuf  
(74) *Attorney, Agent, or Firm* — Simmons Perrine Moyer Bergman PLC (57) ABSTRACT

A method for maintaining and using a high concentration of dissolved copper on a surface of a useful article by providing a copper surface without coatings thereon which increase the wetting angle and which isolate the copper surface and which has a surface roughness between 2 and 50 micro inches Ra, so as to kill microbes thereon.

6 Claims, 7 Drawing Sheets

(56) References Cited

U.S. PATENT DOCUMENTS

| | | |
|---|---|---|
| 6,638,431 B2 | 10/2003 | Back et al. |
| 6,797,743 B2 | 9/2004 | McDonald et al. |
| 6,929,705 B2 | 8/2005 | Myers et al. |
| 7,163,709 B2 | 1/2007 | Cook et al. |
| 2008/0118540 A1* | 5/2008 | Roe et al. .................. 424/405 |

OTHER PUBLICATIONS

Gadi Borkow and Jeffrey Gabbay, The FASEB Journal Express Article 10.1096/fj.04-2029fje. Published online Sep. 2, 2004. "Putting copper into action: copper-impregnated products with potent biocidal activities".

* cited by examiner

E-coli Viability on C110 Alloy Surface (Modified Data)

Date: 5/17/07

| Sample | Expose Time (minutes) with E-coli | | | | | | | |
|---|---|---|---|---|---|---|---|---|
| | 0 | 5 | 15 | 30 | 45 | 60 | 75 | 90 |
| Commercial w/BTA | 2,175,000 | 1,192,857 | 1,238,125 | 395,000 | 250,000 | 192,583 | 85,000 | 41,083 |
| Process 4 | 946,250 | 104,313 | 141,000 | 35,375 | 3,700 | 1 | 1 | 1 |

FIG. 6

E-coli Viability on C110 Alloy Surface (Modified Data)

Date: 5/17/07

| Sample | Expose Time (minutes) with E-coli | | | | | | | | |
|---|---|---|---|---|---|---|---|---|---|
| | 0 | 5 | 15 | 30 | 45 | 60 | 75 | 90 |
| Commercial w/BTA | 2,175,000 | 1,192,857 | 1,238,125 | 395,000 | 250,000 | 192,583 | 85,000 | 41,083 |
| Process 5 | 2,896,667 | 538,750 | 622,500 | 156,250 | 35,000 | 1 | 1 | 1 |

FIG. 7

METHODS OF MAINTAINING AND USING A HIGH CONCENTRATION OF DISSOLVED COPPER ON THE SURFACE OF A USEFUL ARTICLE

The invention claims the benefit of priority of U.S. Provisional Patent Application No. 60/747,948, "METHODS OF PRODUCTION AND USE OF ANTI-MICROBIAL COPPER", filed on May 23, 2006.

FIELD OF THE INVENTION

The invention relates generally to methods for increasing the concentration of dissolved copper ions and copper containing molecules in solutions disposed on copper and copper alloy surfaces and thereby enhancing the antimicrobial properties of such copper alloy surfaces. Particularly, it relates to methods which can be practiced on an industrial scale prior to fabrication into semi-finished and finished goods, as well as treatments which can be applied after fabrication.

BACKGROUND OF THE INVENTION

Copper and copper alloys have been used for millennia as some of mankind's primary technological materials. Their combination of ease of manufacture, recyclability, resistance to overall corrosion, and their availability on a variety of attractive colors and finishes have made them the preferred material for coinage, as well as a variety of artistic and architectural applications where these properties are important. Electrical and thermal conductivity greater than nearly all competitive materials combined with useful strength, formability, and relatively low cost have made these materials vital to the electronics industry.

Copper is an essential trace mineral, vital to the health and proper functioning of human metabolism, as well as other life forms at very low concentrations.

Copper sheathing of ships' hulls was used by the British Navy beginning in the $18^{th}$ century to prevent attack by teredo (shipworm) and to prevent attachment of marine weeds and organisms such as barnacles to wooden-hulled ships. The beneficial effects were due to slow dissolution of the copper surface in contact with seawater. Also, copper and copper compounds have been used in paints for ships' hulls made of a variety of materials for their effectiveness in preventing fouling of ships' bottoms by marine organisms. These anti-fouling properties are tied to the release of copper ions from the affected surface, resulting in a microenvironment at the surface which is toxic to such organisms and preventing attachment of these organisms to the affected surface. Marine microorganisms may be affected by as little as 1 part per billion copper (1 ppb Cu).

Recent studies have shown that copper alloy surfaces are effective at decreasing the viability of microorganisms such as *salmonella, listeria,* and *E. coli* which cause food-borne illnesses. Such surfaces are also effective at reducing viability of microorganisms tied to secondary infections in health care facilities, such as *staphylococcus aureus, legionella,* and others.

Traditionally, copper alloy products are produced with a bright surface protected from oxidation by a variety of treatments. Copper and copper alloys will naturally form a thin oxide layer in contact with the atmosphere, consisting primarily of cuprous oxide ($Cu_2O$) at normal temperatures; in environments containing sulfur, there is an increased proportion of cupric oxide (CuO) and cupric sulfide (CuS). This layer will grow thicker over time, eventually obscuring the bright surface and causing the surface to darken. Dark films of oxides and/or sulfides on the surface are considered "dirty" and objectionable, unless used deliberately for specific decorative or architectural purposes. A great deal of effort and research has gone into methods of preventing such films from forming and of removing them when they do form. Application of surface treatments (anti-tarnish films, stain inhibitors, or polymer coatings) which slow the transport of oxygen to the copper alloy surface also slows formation of oxide films. These and other methods are well known to those skilled in the art.

Since the antimicrobial properties of copper, copper alloys and copper compounds have been known for some time, there have been a number of patents issued for materials and processes making use of these properties. As noted above, copper sheathing has been used for centuries to prevent biofouling of ship hulls; more recently, static underwater structures such as oil platforms have been similarly protected. Galvanic corrosion between the steel of the platforms and the protective copper sheathing has limited the usefulness of this method, but Miller (U.S. Pat. No. 4,987,036; 1/1991) discloses a method of creating a substantially continuous coating by placement of numerous small platelets of copper adhered to the structure with an electrically insulating material. Inoue (U.S. Pat. No. 5,338,319; 2/1995) discloses a related method for coating the inside of a resin pipe with a beryllium-containing copper alloy. Both methods involve contact with seawater.

Another patent (Miyafuji U.S. Pat. No. 6,313,064; 11/2001) makes use of a Cu—Ti alloy where the titanium (and possibly other alloying elements) preferentially oxidizes. Although this does rely on a deliberate surface treatment to produce oxides and available ions at the metal surface, these oxides and ions include other and more reactive elements than just copper sulfides and oxides and copper ions.

Many patents have been issued for copper-containing biocides for use on agricultural produce and in water treatment. Copper salts and compounds provide a strong source of antimicrobially effective copper ions, but the relatively high solubility of the compounds results in short periods of effectiveness before the copper is washed away. Many of the patents focus on methods to decrease the release of copper into solution and increase the effective lifetime of the treatment. Examples of this type of product are given in Cook (U.S. Pat. No. 7,163,709; 1/2007), Back (U.S. Pat. No. 6,638,431; 10/2003), Stainer (U.S. Pat. No. 5,171,350; 12/1992), and Denkewicz (U.S. Pat. No. 6,217,780; 4/2001). These treatments may be applied to a variety of surfaces, but they do not make use of a permanent, inherently antimicrobial copper or copper alloy surface to act as a long-term source of copper ions.

Another method used to make metallic mill products (such as metal sheet or strip in coils) with an antimicrobial surface is to coat the surface with a solution, paint, or polymer containing an antimicrobial agent and dry or cure the coating in place. The antimicrobial agent may be metallic particles, non-metallic particles carrying antimicrobial metal ions, glass particles containing such ions, and/or particles of metal salts or similar compounds. The classic example of these methods is the "HealthShield" product line from AK Steel (Myers, et al.; U.S. Pat. No. 6,929,705; 8/2005), consisting of a metallic substrate coated with a resin formulation carrying inorganic zeolites and oxides which in turn carry metal ions or compounds for antimicrobial effect. Other similar products (directly using metal compounds or salts) are disclosed in Lyon (U.S. Pat. No. 6,042,877; 3/2000) and Zlotnik (U.S. Pat. No. 5,066,328; 11/1991), although this list is by no means exhaustive. While these coatings may be applied to a number of different substrates, either before or after fabrication into finished articles, the antimicrobial properties of these items are due to the coating alone and do not rely on the metallic article itself as a permanent source of antimicrobial ions.

Yet another method of forming antimicrobial articles and surfaces also involves the use of particles of metal powders, metal-ion containing salts and other compounds, and metal-ion carrying particles similar to those noted above, but blended throughout a bulk polymer or similar moldable substance. McDonald (U.S. Pat. No. 6,797,743; 9/2004) discloses such a polymer, also used as a coating on a substrate item; Kiik (U.S. Pat. No. 6,585,813; 7/2003) discloses a related formulation used to fight algae growth on blended asphalt roofing shingles and other items used in the building trades. Again, the anti-microbial properties are due to the copper- or other metal-containing particles, and not due to the bulk of the material itself. Also, the effectiveness of these materials is limited by the total concentration of anti-microbial metal particles and compounds which can be blended into the matrix, and by transport of these effective ions through the matrix to the useful surface, where an uncoated metal surface presents the effective ions directly at the surface with minimal transport and concentration limited only by the solubility of the metal in the solution of interest.

One disadvantage of the traditional method of supplying copper surfaces free of oxidation and treated to prevent further oxidation is that a clean, bare, bright copper surface is generally hydrophobic, minimizing or preventing contact between the surface and water or aqueous solutions. Treatments normally applied to prevent further oxidation are generally even more hydrophobic than the original copper surface, both directly minimizing physical transport of oxygen to the copper surface and preventing formation of adsorbed films of water on the surface which can assist transport of oxygen to the surface and copper ions from the surface.

A further disadvantage of such treatments is that clean, bare, bright copper in the metallic, non-ionized state is nearly insoluble in water. Oxidation of copper provides copper ions which can be assimilated into aqueous solutions or into body fluid residues to provide antimicrobial properties. Without such copper ions available for transport, an antimicrobially active surface would need to develop naturally. Not only can these natural/atmospheric processes be slow to occur, but the reactions required are variable in reaction time, dependent on the nature of prior commercial treatment, environmental conditions, and, therefore, are difficult to predict. One interested in ensuring that a surface is active at the time it is placed in service would benefit from the stated invention(s), as they ensure the surface is predictably active at the time it is placed in service. It is, therefore, difficult to predict the antimicrobial activity of these naturally formed surfaces.

Prior art does not address the effects of manufacturing methods necessary to create commercially useful articles and how those stated antimicrobial surfaces could be changed in processing. The invention is directed to the problem of creating a repeatably and renewably active surface at the time an article is placed in service which provides copper ions available for assimilation into aqueous solutions or body fluid residues for antimicrobial properties, which can be produced on semi-finished goods or finished articles during or after manufacture.

SUMMARY OF THE INVENTION

In one embodiment, the present invention creates a specific surface finish on copper and copper-alloy surfaces by any of a variety of methods, which may be followed by chemical treatment to increase concentrations of dissolved copper ions in solutions in contact with the surfaces and thereby enhance the microbial properties of the surfaces. The surface finish may be produced by cold rolling with work rolls of suitable finish; by grinding with suitable abrasives; by brushing or buffing with or without abrasives; by impacting the surface with grit or shot of suitable size and velocity; by controlled chemical etching; and a number of other different processes. The purpose of the specific surface finish is to enhance wetting of the copper alloy surface by water, aqueous solutions, and/or bodily fluids to enhance dissolution of copper and copper ions into said fluids for antimicrobial effect.

In one embodiment, the chemical treatment involves the use of a degreasing treatment during mill coil processing to remove oils, greases, waxes, and other surface contaminants which will interfere with wetting of the surface by aqueous solutions or bodily fluids. It may also involve further treatment of the degreased surface with diluted acid, possibly with the addition of an oxidizing agent, followed by a water rinse. This further treatment is used to change the oxidation state of the copper or copper alloy surface to enhance takeup of copper ions from the surface into solutions in contact with the surface.

In one embodiment, the chemical treatment of the surface specifically does not include application of tarnish inhibitors such as benzotriazole (BTA) or tolytriazole (TTA), or of films of oils, waxes, or other substances used to inhibit wetting of the surface by water, aqueous solutions, or bodily fluids or to slow or prevent transport of oxygen or sulfur to contact with the copper or copper alloy surface. Such applications inhibit takeup of copper ions from the treated surface and decrease the antimicrobial properties of the surface.

Accordingly, the present invention comprises a useful article comprising a copper alloy surface configured to continuously provide a source of copper to be dissolved in high concentrations into a solution disposed on the copper alloy surface.

BRIEF DESCRIPTION OF THE DRAWINGS

FIG. 1 shows measured contact angle as a function of process and alloy. The contact angle is higher for commercial treatments with anti-tarnishing agents such as BTA, TTA, and oil than it is for either of the invented processes listed. A commercially treated surface with an oil film has the highest contact angle and least wetting by water. A surface treated with acid and an oxidizing agent such as hydrogen peroxide (Process 2) exhibits a low-contact angle and good wetting. This pattern holds for all alloy families listed (copper, red brasses, and yellow brasses).

FIG. 5 shows results for treatment by invention Process 4. This process shows a 3 $\log_{10}$ reduction in CFU after 45 minutes exposure, with complete inactivation after 60 minutes. Commercial material shows only a slight reduction after 90+ minutes exposure.

FIG. 6 shows results for treatment by invention Process 5. This process shows a slightly lower (2 $\log_{10}$) reduction in CFU after 45 minutes exposure, with complete inactivation after the same 60 minutes. Commercial material shows only a slight reduction after 90+ minutes exposure.

DETAILED DESCRIPTION OF THE INVENTION

The invention can better be understood by reference to the following detailed description wherein numerous exemplary processes are described. Numerous abbreviations are used throughout. To aid in the understanding, some of the abbreviations are described and listed in Table 1 below. These definitions relate to numerous matters, including but not limited to detailed definitions of materials, material characteristics, tests procedures, innovative manufacturing and surface treatment processes and other processes of the present invention.

TABLE 1

Process Conditions/Definitions

| | |
|---|---|
| Finish A = | 6-14 Ra rolled, typically 10 Ra |
| Finish B = | 2-5 Ra rolled, typically 4 Ra |
| Finish C = | 18-40 Ra rolled, typically 28 Ra |
| MILL OIL = | As-rolled; remnants of rolling lubricant. NOT degreased; starting point for other conditions. |
| DG = | Degrease using commercial solution |
| DRY = | Forced air dry |
| PKL = | 10-20% $H_2SO_4$ + 1-3% $H_2O_2$ |
| RT = | Age 72 hours @ 25° C. in air |
| FURN1 = | Furnace treat 2 hours @ 200° C. in air |
| FURN2 = | Furnace treat 5 minutes @ 400° C. in air |
| Process 1 | DG + DRY |
| Process 2 | DG + PKL + DRY |
| Process 3 | DG + DRY + RT |
| Process 4 | DG + DRY + FURN1 |
| Process 5 | DG + PKL + DRY + FURN2 |

1) Contact Angle Studies—Surface Wetting by Aqueous Solution

One measure of the effectiveness of the treatments according to the present invention is to determine the contact angle between the treated surface and the top surface of a water drop sitting on the surface ("sessile drop"). In this detailed description, the contact angle is defined as the angle of incidence between the solid surface and the liquid, both in the presence of air. Physically, this corresponds to the angle between the solid surface itself and a plane tangent to the droplet surface at the point of contact between solid, liquid, and air. This contact angle is related to surface interface energies and the chemical bonding of the surfaces involved, as seen by wettability of the surface by various fluids and adhesion between surfaces. These surface energies (and contact angles) are in turn related to such controllable factors as surface roughness (Ra); the chemistry of the base surface itself; the presence or absence of surface films or layers of oxides, sulfides, etc. (and their type); and the thickness of such surface films.

In this invention, the solid surface in question is a permanent metallic surface of copper alloy, either as part of a bulk metal object or as a thinner layer (but still permanent) deposited on a substrate. "Copper alloy" is used herein to refer to any copper containing alloy including just copper itself. The contact angle measurements discussed herein were performed with a single standard fluid, lab-quality filtered deionized/reverse osmosis water (DI/RO water) which had been boiled to minimize and stabilize the dissolved gas content of the liquid. Measurements were made on a variety of metallic surfaces treated according to the invention processes, using the sessile drop method. The actual measurements of contact angle were made using a real-time capture camera/microscope setup. Drop Shape Analysis system). Measurements were taken every second for one minute after dosing the surface with 0.003 ml of the "standard water" noted above. The final contact angle after 60 seconds of contact was selected as the standard for comparison in this study; this helped minimize variability in measurements due to vibration of the test setup, lighting conditions, and air currents.

Figure 1:
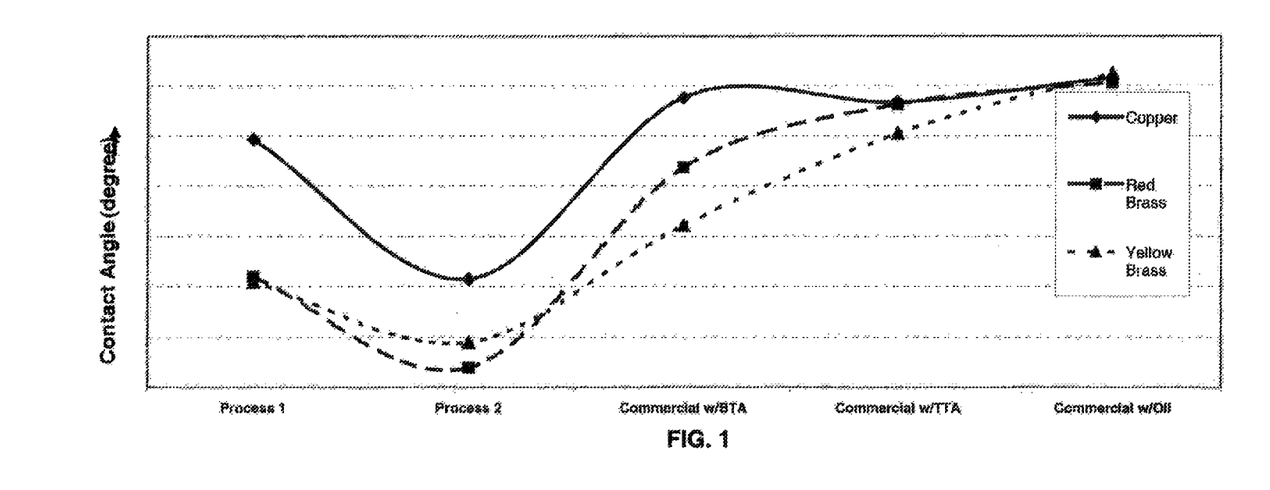

Results of contact angle measurements are shown in FIG. 1. Commercially processed material with an oil film remaining on the surface has the highest contact angle and thus poorest wetting by the water used for the test. This is expected, since it is a common observation that "oil and water do not mix". Commercial surfaces treated with hydrophobic tarnish inhibitors tolytriazole (TTA) and benzotriazole (BTA) also exhibit high contact angles and poor wetting, meaning that water (and aqueous solutions such as bodily fluids and many cleaners) will not contact the surface so treated. These results show a similar pattern for different copper alloys, although the actual data varies; results for copper, red brass and yellow brass are given in FIG. 1. Surfaces treated by the first process of the invention, hereafter "Process 1", show a consistently lower contact angle than standard commercial processes for each alloy tested, and surfaces treated by the second invention process, hereafter "Process 2", show contact angles dramatically lower yet.

2) Copper Evolution Testing on Treated Surfaces Using Simulated Body Fluids [Immersion in Artificial Sweat]

As a further measure of the effectiveness of copper alloy surfaces treated according to the invention, tests were performed to determine rates of copper evolution from the metallic surface in simulated bodily fluids. Since one of the primary uses of such treated surfaces is in prevention of cross-contamination between infected and un-infected hospital personnel, touch surfaces such as push plates and door handles contacted by the skin of the hands (and thus by fluids such as sweat) are of particular interest. A search of the published literature shows a great deal of interest in metal evolution in human sweat, in large part due to incidents of contact dermatitis. As such, there are a number of formulations of "artificial sweat", although there are few in published standard test methods and these appear to be primarily directed at testing for nickel (Table 2). Common to nearly all of the formulations investigated is the presence of salts, lactic acid, and some nitrogen-containing substance simulating the amino acid residues found in actual sweat. The proportions vary widely, although most are similar to commonly used blood plasma extenders, and many formulations include other substances (such as sulfides, ammonia, or ammonia salts) which would be expected to react strongly with copper surfaces.

ICP testing, did not permit agitation of the solution on the surface, and resulted in greater variability of the test results

TABLE 2

Artificial Sweat Formulations

| Component | ISO 3160-2 | EN 1811 | Unknown1 | Denmark | Unknown2 | JIS L0848D | Japan2 | RL-1 (PMX) |
|---|---|---|---|---|---|---|---|---|
| NaCl | 20 g/l | 0.50% | 7.5 g/l | 4.5 g/l | 0.30% | 19.9 g/l | 17.0 g/l | 6.0 g/l |
| KCl | | | 1.2 g/l | 0.3 g/l | | | | 0.3 g/l |
| Urea | | 0.10% | 1.0 g/l | 0.2 g/l | 0.20% | 1.7 g/l | 1.0 g/l | 2.0 g/l |
| $C_3H_6O_3$ Lactic Acid | 15 g/l | 0.10% | 1.0 ml/l | | 0.20% | 1.7 g/l | 4.0 g/l | |
| $NH_4Cl$ | 17.5 g/l | | | 0.4 g/l | | 0.2 g/l | | |
| Acetic Acid | 5 g/l | | | | | | | |
| $Na_2SO_4$ | | | | 0.3 g/l | 0.10% | | | |
| Na2S | | | | | | 0.8 g/l | | |
| $CH_3OH$ Methanol | | | | | | | 1500 ml | |
| $NaC_3H_5O_3$ Sodium lactate | | | | | | | | 3.1 g/l |
| pH | 4.7 | 6.6 | 4.57 | not specified | 4.5 | not specified | not specified | not specified |
| adjusted by | NaOH | NH4OH | not specified | not specified | not specified | not specified | not specified | not specified |

One artificial sweat formulation selected for this testing is found in JIS L0848D, which includes both $NH_4Cl$ (ammonium chloride) and $Na_2S$ (sodium sulfide). Both of these would be expected to significantly corrode copper surfaces, as well as being somewhat toxic to micro-organisms in their own right. Subsequent testing with this formulation showed unexpected corrosion and formation of insoluble films of CuS (copper sulfide). This corrosion product would be difficult to analyze for by the selected technique, as well as being in a non-bioavailable form and thus ineffective from an antimicrobial standpoint, so testing with this formulation was discontinued. The other composition used is a compromise between other less aggressive formulations found in the literature, and is based on readily available medical supplies. This formula (referred to as "RL-1") is made by taking Lactated Ringer's solution (a common blood plasma extender used in cases of severe dehydration or blood loss) and adding urea in quantities adequate to simulate the amino acid residues and protein breakdown products normally found in actual sweat. The final composition is also given in Table 2.

Copper samples were exposed to artificial sweat by two methods (immersion and sessile drop) Immersion testing consisted of placing a treated metal coupon into a large test tube with a known quantity of the selected sweat formulation (generally 15 ml, sufficient to completely cover the sample). The tube was agitated for the desired exposure time, after which it was removed from the tube and rinsed down into the tube with a known quantity of lab-quality filtered deionized/reverse osmosis water (DI/RO water). The total amount of artificial sweat used was noted for calculation of dilution factors to determine actual concentration of copper in the original exposure. The sessile drop method ("drop" testing) consisted of pipetting a small quantity of the test solution onto the top surface of a treated coupon held horizontally, exposing for the desired time, then dumping the droplet into a test tube and rinsing the coupon into the tube with a known quantity of DI/RO water. The quantity of solution which could be used for the initial droplet exposure was limited by the surface tension of the solution on the treated coupon. This method (while similar to the subsequent biological test exposure procedure) had less copper surface area exposed to the solution, required greater dilutions to provide sufficient volume for than the immersion test method. Copper evolution results presented here are all by the immersion technique.

The exposed and diluted solutions were analyzed for copper content by inductively coupled plasma spectroscopy (ICP) on an IRIS Intrepid II XSP Dual View spectroscope from Thermo Electron Corporation. The copper detection limit for this machine was 1.3 parts per billion (PPB). This is of the same order as the minimum toxicity limit for copper in anti-fouling applications in seawater (1 PPB), so the presence of any detectable copper in solution would be expected to indicate some antimicrobial effect, with greater effects at higher Cu concentrations. Dilution levels were used to re-normalize the analyzed concentrations back to the values appropriate during the actual exposures. Analysis was also performed for other elements (Al, Zn, Ni, and Ag) as a check on consistency of testing by ICP.

Figure 2:
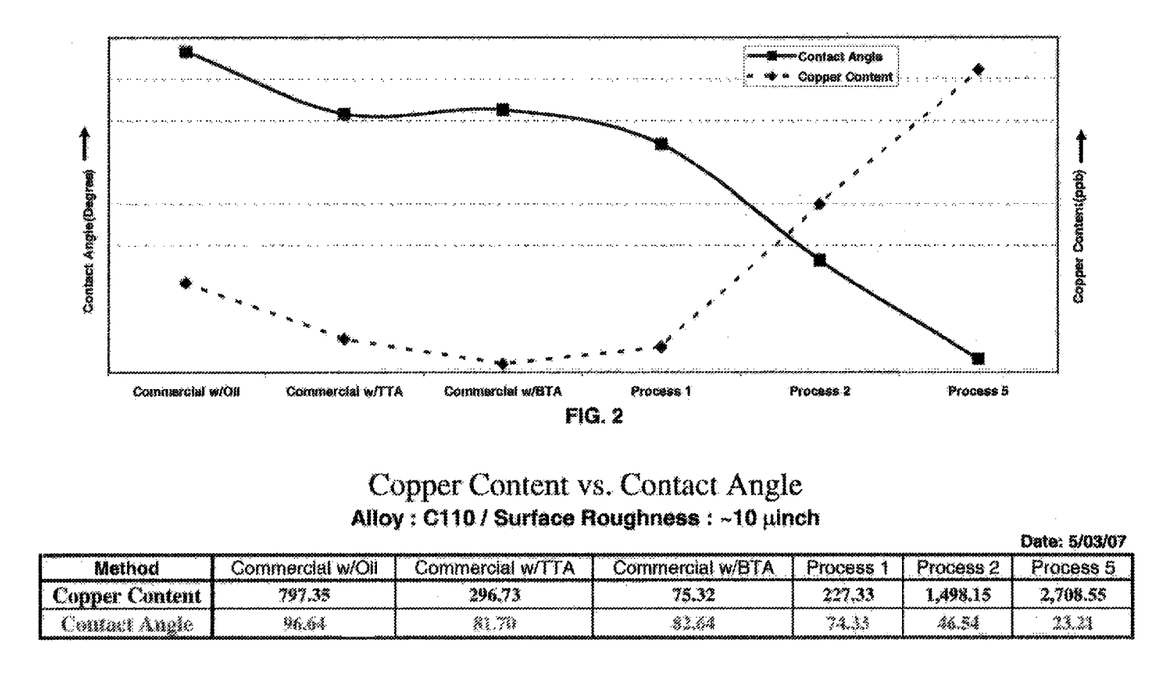
FIG. 2 shows the relationship between copper evolution (dissolution) into aqueous solution and contact angle as a function of surface treatment process. The copper evolution increases with decreasing contact angle, showing that wetting between the surface and the solution (low-contact angles) is important for increased copper evolution and thus antimicrobial effect.

FIG. 2 shows a comparison between contact angle measurements for various process treatments and the copper evolution into solution from coupons treated by the same processes. For normal commercial processes, there is a generally low rate of copper evolution, and there are indications that what copper does show up is tightly bound and not available for microorganisms. For surfaces treated by the processes of the invention, there is a strong correlation between contact angle and copper evolution; as the contact angle decreases (indicating better wetting of the surface), the copper evolution increases dramatically.

Figure 3:
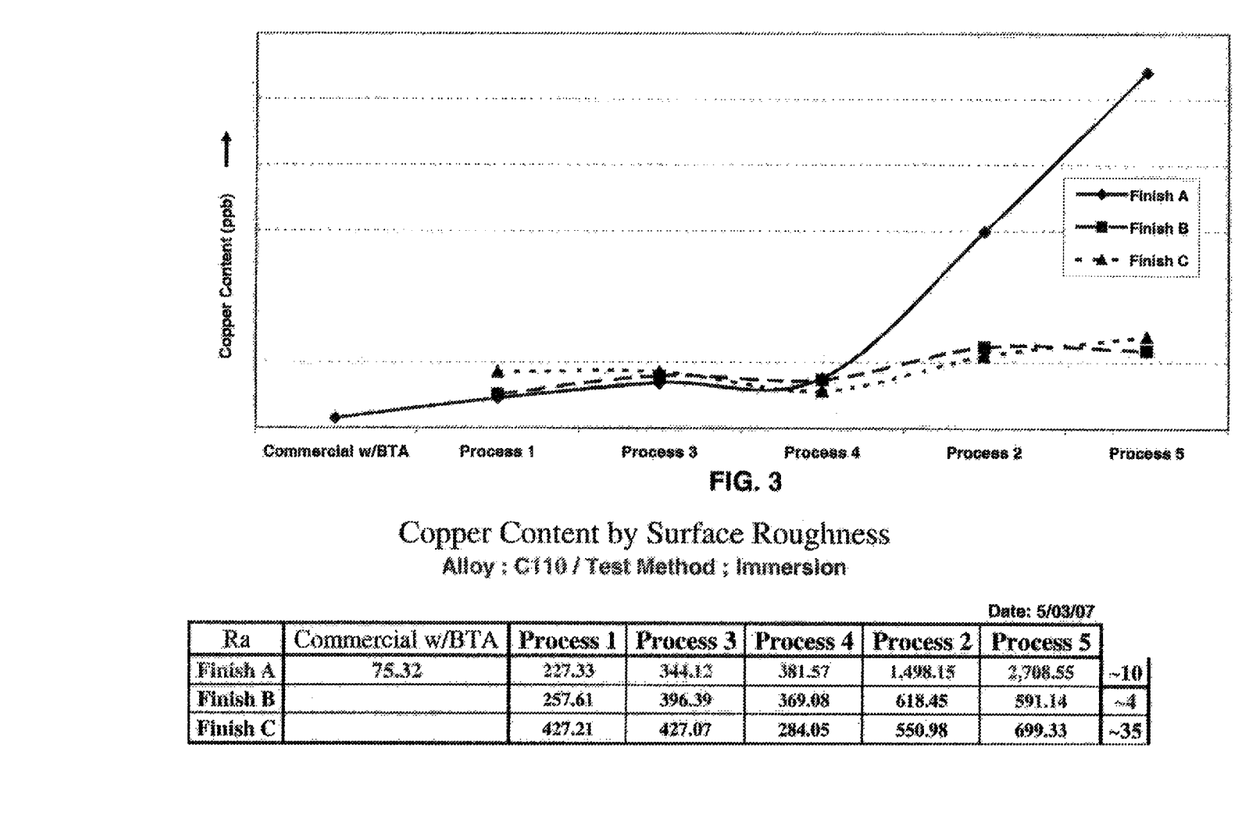
FIG. 3 shows copper evolution/content in solution as a function of process route and surface finish. All invention processes show increased copper in solution compared to normal commercial processing with BTA as a tarnish inhibitor. For surface finish "A" (the preferred embodiment), certain process routes show dramatic increases in copper evolution into solution. The combination of Process 5 and Finish A showed the highest copper release of methods tested.

Results of copper evolution into solution from treated coupons immersed in artificial sweat RL-1 for various processing routes and surface finishes are given in FIG. 3. Copper contents in solution for all processes associated with this invention are higher than the results obtained from standard commercial processing of strip with a benzotriazole (BTA) tarnish inhibitor coating. For surface finishes B and C, results follow a similar pattern for all processes tested (2-6 times increase in Cu content over the standard commercial process). For surface finish A (the preferred embodiment), results are similar to other surface finishes for some invention process routes, but other preferred process routes (Process 2 and Process 5) show dramatic improvements, from 15 times to 25+ times increases in copper content in solution.

3) Microbiological Testing—Inactivation of Bacteria Exposed on Treated Copper Alloy Surfaces A further confirmation of the antimicrobial effectiveness of the processes of the invention is actual testing with biological agents to show the rates at which such agents are inactivated by contact with treated surfaces. The test method used is a modification of an ASTM-approved method for the evaluation of the antimicrobial effectiveness of sanitizers on inanimate, nonporous, non-food-contact surfaces. The method used consisted of:

1) Preparing a standard culture of the micro-organisms to be tested;
2) Securing samples of the desired materials, and/or treating the samples according to the desired test conditions (the processes of the invention and standard materials for comparison);
3) Exposing the treated samples to a known quantity of the cultured organisms for the desired test time;
4) Placing the exposed coupon in a quantity of an appropriate neutralizing solution (which will neither encourage nor discourage further growth of the organisms and will neutralize further effect of the tested surface) and ultrasonically treating the coupon to suspend any surviving organisms into the neutralizing solution;
5) Removing the test coupon from the neutralizing solution to further ensure stopping of the antimicrobial effects of the copper alloy surface;
6) Diluting the neutralizer solution (with surviving micro-organisms) to an appropriate level to give readily-countable results after exposure, and exposing a known quantity of the diluted solutions on Petri dishes coated with a suitable growth medium for the organisms selected;
7) Incubating the exposed plates (prepared Petri dishes) to encourage growth of countable colonies, followed by counting the colonies on individual plates;
8) And calculating (based on the known quantities of solutions transferred and dilution levels) the number of colony-forming units (CFU's) in the original solution used to remove the surviving organisms from the exposed surface;
9) To provide baseline data for comparison, a matching quantity of the original standard culture is treated by identical techniques (except for exposure to the copper alloy surface), plated, incubated and counted by the same methods.

Duplicate coupons of alloy C11000 with surface finish A (~10 Ra) were tested for each test condition, and all dilutions were also plated in duplicate to minimize the effects of variations in biological laboratory preparation techniques. All exposures in this study were performed using *Escherichia coli* (ATCC 11229) obtained from the American Type Culture Collection (ATCC), Manassas, Va. Similar results are expected using other organisms of interest, such as *Staphylococcus aureus* and *Salmonella enterica*, which have been implicated in outbreaks of hospital-acquired (nosocomial) infections and food poisoning. Stock cultures were incubated for at least 48 hours before use, to ensure vigorous growth of the organisms. Twenty micro-liters of stock culture were used for inoculation of the treated coupons, and the survivors were suspended in 20 ml of Butterfield's buffer solution (0.6 mM $KH_2PO_4$ monopotassium phosphate in DI/RO water) as a neutralizing agent. The same buffer was also used for subsequent dilutions, and final growth plates were inoculated with 20 ml of the diluted suspensions. The growth medium for the stock cultures of *E. coli* was Difco™ Nutrient Broth (beef extract and peptone) and the medium for the Petri dishes (plate medium) was Difco™ Nutrient Agar, both from Becton, Dickinson and Company, Sparks, Md. Sterilization (where appropriate) was by means of steam autoclave (preferred), dry heat in an oven at 200-400° C. (where required for certain test conditions), or by immersion of instruments in 99%+ isopropyl alcohol. Plate counts were performed manually by visual examination of the exposed plates after 48 hours incubation. Plates exhibiting 20-300 colonies (at a particular dilution) were used for counting where possible; lower count plates were used at low dilutions where necessary.

For the purposes of this study, the absolute numbers of bacteria (CFU's) remaining on the coupons after exposure are not as important as the rate of reduction (percentage or $log_{10}$ decrease) from the original baseline number. EPA efficacy data requirements state that a 99.9% reduction in numbers of organisms (3 $log_{10}$ reduction in CFU) be obtained as compared to the baseline to be considered effective, so this was the trigger level sought in the study. The exposure time required for a 3 $log_{10}$ reduction in CFU was determined and compared to similar data from other studies of the antimicrobial effectiveness of copper alloys not treated by the methods of this invention.

Figure 4:
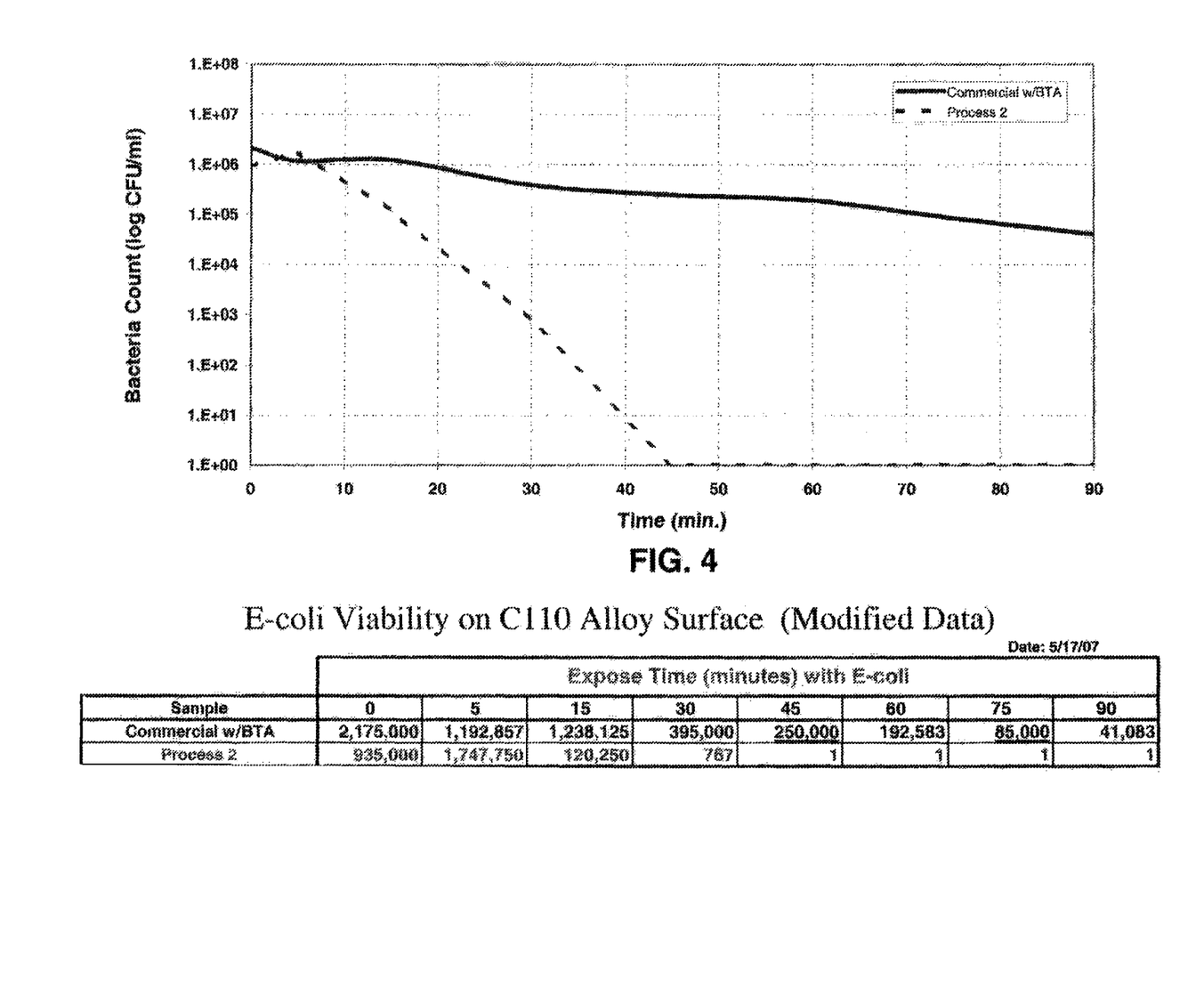
FIG. 4 shows inactivation rates for *E. coli* exposed on surfaces treated by invention Process 2 compared with normal commercially processed material with BTA as a tarnish inhibitor. This process shows a 3 $\log_{10}$ reduction in CFU (99.9% reduction in active bacteria) after only 30 minutes exposure, with complete inactivation after 45 minutes. Commercial material shows only a slight reduction after 90+ minutes exposure.

Results of microbiological exposure testing are presented in FIG. 4 through FIG. 7. In all cases, results of exposures using one of the processes of the invention are compared against exposures of samples treaded using normal commercial processing and coated with BTA as a tarnish inhibitor film, a normal condition for copper alloy mill products. FIG. 4 shows the results of treatment by invention Process 2 (DG+PKL). Surfaces treated by this process show a 3 $log_{10}$ reduction in CFU (99.9% reduction in active bacteria) after only 30 minutes exposure, with complete inactivation after 45 minutes. Commercially processed material with a BTA coating shows only a 2 $log_{10}$ reduction in CFU after 90 minutes exposure (the longest used in this study). In a 2005 study, Michels et al. shows complete inactivation of a different strain of *E. coli* after 90 minutes, although surface finish and presence of any anti-tarnish films is not reported.

Figure 5:
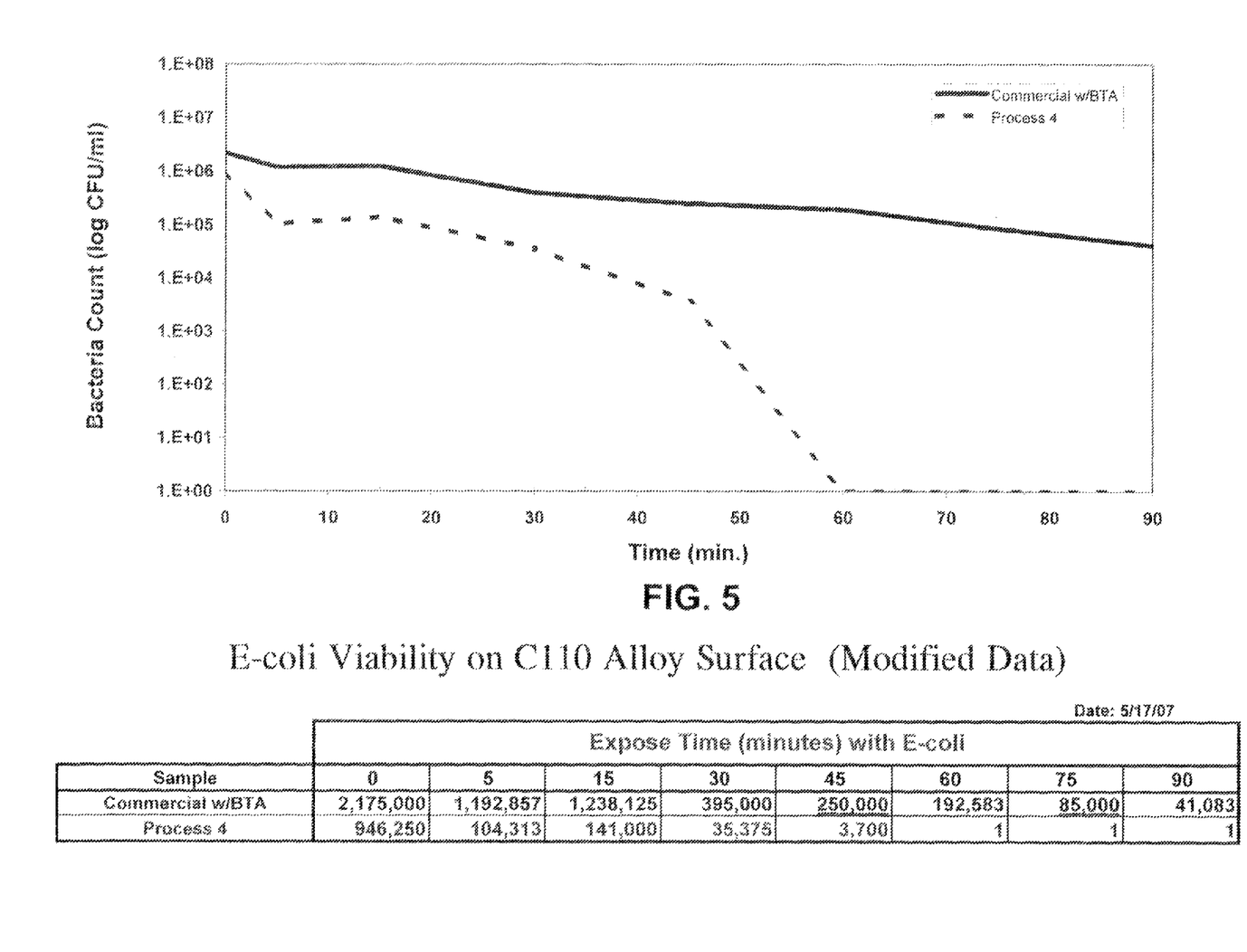

FIG. 5 shows results of biological exposures using invention Process 4 (DG+PKL+FURN1). Surfaces treated by this process show a 3 $log_{10}$ reduction in CFU at slightly more than 45 minutes, with complete inactivation after 60 minutes exposure.

Figure 6:
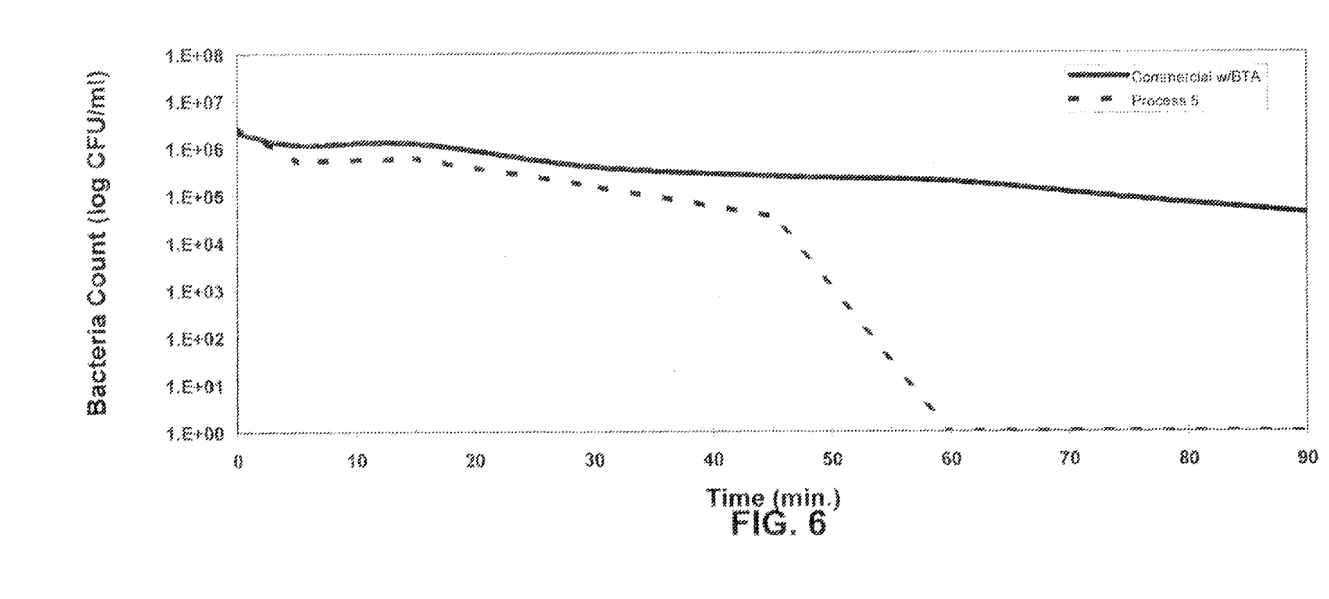

FIG. 6 shows results of biological exposures using invention Process 5 (DG+PKL+FURN2). Surfaces treated by this process show a lower reduction in CFU at 45 minutes (only 2 $log_{10}$ reduction), but a sharp transition and complete inactivation after the same 60 minutes exposure. All three of the preferred processes tested show a significantly faster reduction in active CFU's (40-60% less time to 3 $log_{10}$ reduction and 30-50% less time to complete inactivation) compared to previously published data.

Figure 7:
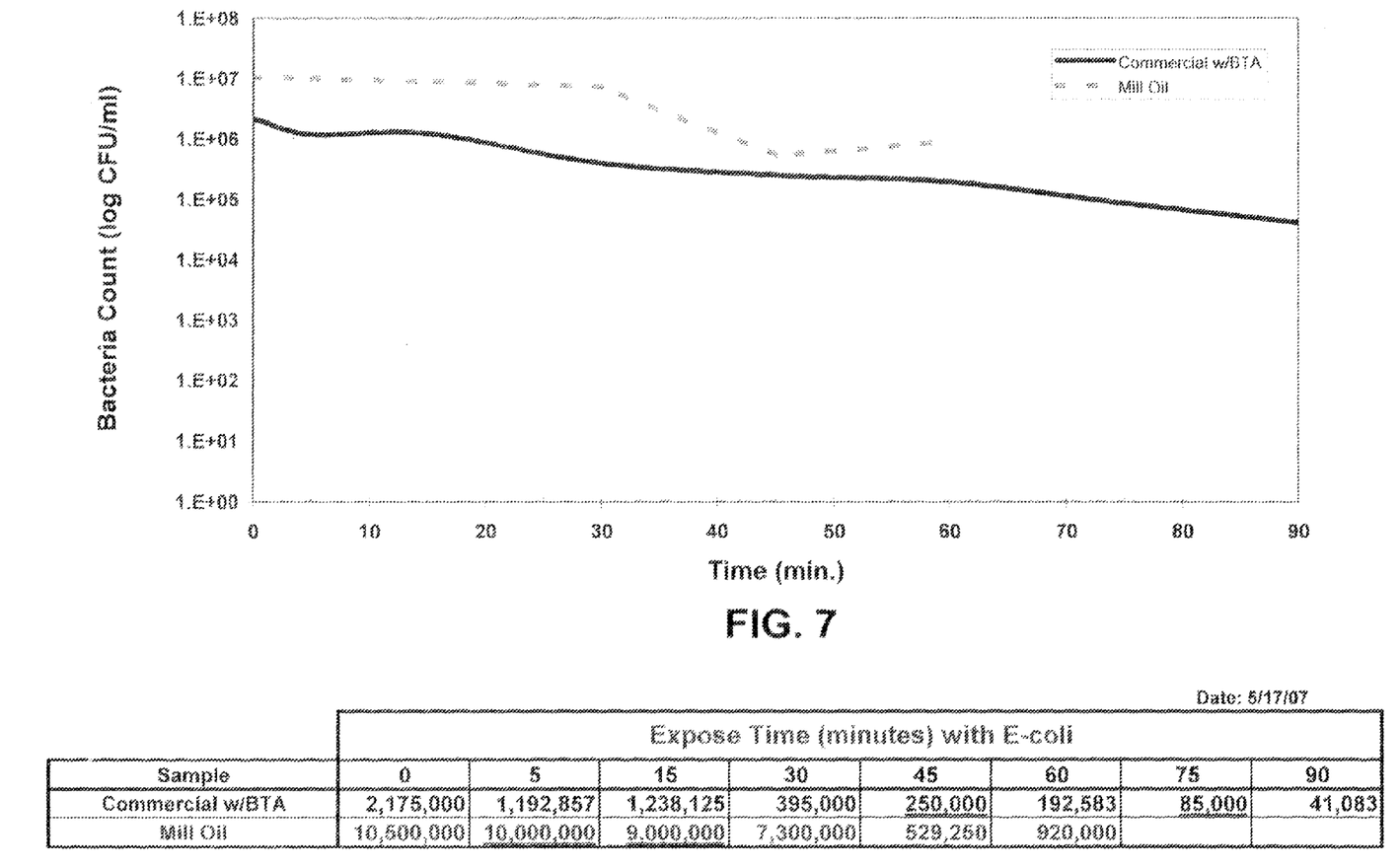
FIG. 7 compares commercially processed material with BTA and rolled material with a residual oil film and no further processing. Both "commercial conditions" exhibit substantially low rates of inactivation of the bacteria through the tested times when compared to the present invention.

FIG. 7 shows a comparison between the standard final commercial processing (including BTA as a tarnish inhibitor) and material rolled, but not cleaned or coated, with a residual film of rolling mill lubricant. These two conditions show similar behavior, with low rates of inactivation of the exposed bacteria (only 1-1.5 $log_{10}$ reduction in CFU after 60-90 minutes). Contact angle studies showed both of these conditions had poor wetting and high contact angles, and the mill oil samples had the highest contact angle studied.

One embodiment of the invention shall be further described by reference to the following example:

Copper alloy strip is processed to the desired thickness, annealed to soften and cleaned by normal processes to remove oxides from the strip prior to final rolling. Work rolls with surfaces intended to give the desired surface finish are loaded into the rolling mill stand; the strip in coil form is loaded into the rolling mill and rolled to the final thickness in one or more passes. The surface finish required on the work rolls to result in the desired surface finish will depend on the alloy, incoming hardness, incoming surface finish, reduction pass schedule, and other factors known to those skilled in the art. The desired surface finish of the rolled strip should be between 2 and 50 micro inches Ra; preferably this finish should be between 4 and 36 micro inches Ra; and most preferably between 6 and 14 micro inches Ra. Following rolling, the strip in coil form is loaded onto a semi-continuous cleaning line and the residual rolling lubricants removed using a commercial degreasing solution, rinsed with water (without application of a hydrophobic tarnish inhibitor), and dried with hot air. The dried strip discharging from the cleaning line is formed back into a coil for ease of transport. Slitting to final width and packaging for shipment should be performed with minimal delays to prevent excess atmospheric oxidation of the uncoated strip which may be visually objectionable to the customer. Normal tarnishing and slight oxidation of the strip surface is expected as part of the process and may be beneficial to antimicrobial properties of the strip. Cleaning may be performed either with or without brushing or buffing, as needed to further refine the surface finish.

A further embodiment of the invention shall be described by reference to the following example:

Copper alloy strip is processed to the desired ready-to-finish thickness, annealed to soften and cleaned by normal processes to remove oxides from the strip prior to final rolling. Work rolls with surfaces intended to give the desired surface finish are loaded into the rolling mill stand; the strip in coil form is loaded into the rolling mill and rolled to the final thickness in one or more passes. The surface finish required on the work rolls to result in the desired surface finish will depend on the alloy, incoming hardness, incoming surface finish, reduction pass schedule, and other factors known to those skilled in the art. The desired surface finish of the rolled strip should be between 2 and 50 micro inches Ra; preferably this finish should be between 4 and 36 micro inches Ra; and most preferably between 6 and 14 micro inches Ra. Following rolling, the strip in coil form is loaded onto a semi-continuous cleaning line and the residual rolling lubricants removed using a commercial degreasing solution, rinsed with water, treated with a solution of acid appropriate to reduce or dissolve metal oxides such as nitric, sulfuric, phosphoric, hydrochloric or similar. Many commercial formulations rely on concentrations of sulfuric acid, typically <30% (to which may be added an oxidizing agent such as hydrogen peroxide), followed by rinsing with water (without application of a hydrophobic tarnish inhibitor), and drying with hot air. The sulfuric acid concentration is preferably <25%, and more preferably 10-20%. Hydrogen peroxide content (if used) is preferably <15% and more preferably 0.5-3%. Other acids and oxidizing agents may be used as well; this example is illustrative only and is not intended to restrict application of the general principles embodied in this invention. The dried strip discharging from the cleaning line is formed back into a coil for ease of transport. Slitting to final width and packaging for shipment should be performed with minimal delays to prevent excess atmospheric oxidation of the uncoated strip which may be visually objectionable to the customer. Normal tarnishing and slight oxidation of the strip surface is expected as part of the process and may be beneficial to antimicrobial properties of the strip. Cleaning may be performed either with or without brushing or buffing, as needed to further refine the surface finish. The cleaning may be performed in a single continuous cleaning line if equipment for both degreasing and acid treatment is available; otherwise, these operations may be performed on two separate cleaning lines. If performed on separate cleaning lines, a hydrophobic tarnish inhibitor may be applied before drying at the first line to provide surface protection to the strip before acid treatment, but no such inhibitor is to be applied following the final treatment step before slitting.)

A further embodiment of the invention shall be described by reference to the following example:

Copper alloy strip is processed by normal commercial methods to a desired surface finish of the rolled strip between 2 and 50 micro inches Ra; preferably this finish should be between 4 and 36 micro inches Ra; and most preferably between 6 and 14 micro inches Ra. The strip may be shipped as-is or degreased, or (if desired for subsequent forming processes) may be annealed to soften and cleaned to remove oxides formed during the annealing process. Following cleaning, the strip may be coated with a hydrophobic tarnish inhibitor to preserve the surface condition and appearance of the strip which is to be formed into finished parts by normal commercial processes such as stamping, drawing, bending, coining, etc. These methods are well known to those skilled in the art. The strip is then formed into finished parts as desired.

Following forming and either before or after final assembly, and prior to placement of the article into service, the article(s) are cleaned with a commercial degreasing solution to remove remnants of oils, waxes, and greases used as forming lubricants and/or rinsed with water (without application of a hydrophobic tarnish inhibitor), and/or dried with hot air. The articles should not have been treated with coatings, lacquers, paints or other polymer finishes prior to said treatment. Subsequent to the degreasing treatment, they may also be treated with an acid solution as noted above. Ex: Sulfuric acid<30% as noted above (to which may be added an oxidizing agent such as hydrogen peroxide) and/or rinsed with water (without application of a hydrophobic tarnish inhibitor) and/or dried with hot air.

The formed parts may also be treated after degreasing to deliberately change the oxidation state of the copper alloy surface, increasing the bioavailability of the copper at the surface to enhance the antimicrobial properties. This may be accomplished by any of a number of methods, including exposure in air (or a reactive atmosphere containing any of a number of constituents such as $O_2$, $H_2$, $N_2$, or compounds of Ag, P, S, N, C, etc.) at temperatures from 0 C up to 500 C for various times; by treatment with solutions of sulfides, halogens, salts and dilute acids; by treatment with water to which oxygen has been deliberately added; by treatment with solutions of hydrogen peroxide or similar oxidizing agents; and other methods known to those skilled in the art. The intent of this treatment is to make the surface more chemically active, rather than the normal commercial practices of preventing oxidation of copper alloy surface.

It should be noted that the above examples are illustrative only, and do not restrict the application of the principles behind this invention. Other specific equipment may be used to achieve the desired surface roughness or finish; other solutions may be used for removal of oils, greases, and other surface films; different acids and concentrations may be used, and oxidizing agents other than hydrogen peroxide may be used as well. The principles of creating a specific desired surface roughness or finish, and/or subjecting the copper alloy surface to a commercial degreasing treatment to remove hydrophobic surface films, and/or treating the surface with acids and/or oxidizing agents to enhance the contact angle between the treated surface and aqueous solutions and increase the bioavailability of the copper in the treated surface, and/or subjecting the surface to a suitable atmosphere and temperature to further enhance the evolution of the copper ions, and/or specifically excluding the used of hydrophobic protective and tarnish-inhibiting films on the surface so treated for antimicrobial effect are the fundamental portions of this invention.

The copper and copper alloy surfaces of the present invention could be used in numerous applications, including but not limited to:

Medical instruments
Appliances
Lighting devices and controls
Plumbing fixtures
Hand tools
First Aid devices
Vehicle touch surfaces
Processing equipment for produce and meat processing
Packaging Agriculture
Grain or food storage
Water/food dispensing
Ear tags
Dairy and meat processing
Fast food and commercial restaurants
Cell phones and telecom
Computers (keyboards and peripherals)
Masks and breathing apparatus
Mold proofing in building products and construction.

Throughout this description the terms degreasing and cleaning are used repeatedly. It should be understood that numerous alternate ways of cleaning/degreasing the surface are contemplated including but not limited to:

1) Abrasively clean/grit blasting
2) Cathodic cleaning/degreasing
3) Anodic cleaning/chemical milling
4) Electrolytically and electrochemically cleaning
5) Application of ultrasonic or other acoustic activation
6) Ion milling for special medical applications In one embodiment it may be preferred to do all of the following:

Use ultrasonic+ a andoic electrolytic clean+ and cathodic chemical milling.

What is claimed is:

1. A method of continuously providing copper to be available to be dissolved in an anti-microbial solution to be in contact with a human hand, the method comprising the steps of:
    a. providing a mass of solid copper alloy having a copper alloy contact surface; wherein the copper alloy contact surface has a surface roughness characteristic and an associated characteristic for killing microbes;
    b. said copper alloy contact surface being free of any barrier coating thereon which covers said copper alloy contact surface, isolates said copper alloy contact surface from exposure to atmospheric oxygen and further provides said copper alloy contact surface with an increased wetting angle;
    c. said copper alloy contact surface being a surface configured to provide a continuous source of copper;
    d. wherein said step of "providing a mass of solid copper alloy having a copper alloy contact surface; wherein the copper alloy contact surface has a surface roughness characteristic and an associated characteristic for killing microbes", comprises the steps of:
    providing a mass of solid copper alloy having a copper alloy contact surface;
    performing at least one of the steps of a and b:
        a. examining and thereafter and therefrom determining that the copper alloy contact surface has a surface roughness within a range of 2 to 50 microinches RA and has a microbe killing characteristic of at least a 99% kill rate of microbes within at most 60 minutes of contact with said copper alloy contact surface; and
        b. configuring the copper alloy contact surface so as to have a surface roughness within a range of 2 to 50 microinches RA;
    configuring said mass of solid copper alloy so as to facilitate exposure of said copper alloy contact surface with a human hand and thereby cause an anti-microbial solution with continuously replenishing copper dissolved therein to be in contact with a human.

2. The method of claim 1 further comprising:
    said step of making a surface roughness determination that the copper alloy contact surface has a surface roughness is that the surface roughness is within a range of 4 to 36 microinches RA and has a microbe killing characteristic of a 99.9% kill rate within 45 minutes of contact with said copper alloy contact surface.

3. The method of claim 2 wherein said useful object is a coin minted by a government and released for distribution and wherein said step of making a surface roughness determination that the copper alloy contact surface has a surface roughness, is that the surface roughness is within a range of 6 to 14 microinches RA, and has a microbe killing characteristic of a 99.9% kill rate within 30 minutes of contact with said copper alloy contact surface.

4. A method of continuously providing copper to be available to be dissolved in an anti-microbial solution to be in contact with a human hand, the method comprising the steps of:
    providing a mass of solid copper alloy having a copper alloy contact surface;
    making, by an examination, a surface roughness determination of the copper alloy contact surface;
    where the surface roughness determination is within a range of 4 to 36 microinches RA;
    making, by an examination, a microbe killing characteristic determination of the copper alloy contact surface;
    said copper alloy contact surface being free of any barrier coating thereon which covers said copper alloy contact surface, isolates said copper alloy contact surface from exposure to atmospheric oxygen and further provides said copper alloy contact surface with an increased wetting angle;
    said copper alloy contact surface being a surface configured to provide a continuous source of copper; and
    directing placement of said mass of solid copper alloy by providing advise of deploying said mass of copper alloy with said copper alloy contact surface with and because of said characteristic for killing microbes into an application configured to facilitate exposure to contact with a human hand or contaminated particles provides for a reduction in live harmful pathogens disposed on said copper alloy contact surface.

5. The method of claim 4 where the surface roughness determination is within a range of 6 to 14 microinches RA.

6. The method of claim 4 wherein said step of making, by an examination, a surface roughness determination comprises the steps of examining the copper alloy contact surface.

* * * * *